US005723340A

United States Patent [19]

Karpf

[11] Patent Number: 5,723,340

[45] Date of Patent: Mar. 3, 1998

[54] OPTICAL INDICATOR FOR DETERMINING THE ACTIVITY OF AN ION IN A SAMPLE

[75] Inventor: Hellfried Karpf, Graz, Austria

[73] Assignee: AVL Medical Instruments AG, Schaffhausen, Switzerland

[21] Appl. No.: 645,891

[22] Filed: May 14, 1996

Related U.S. Application Data

[63] Continuation of Ser. No. 306,421, Sep. 16, 1994, abandoned.

[30] Foreign Application Priority Data

Sep. 30, 1993 [AT] Austria ................................ A-1970/93

[51] Int. Cl.$^6$ ........................... G01N 33/20; G01N 31/22

[52] U.S. Cl. ................................ 436/79; 436/73; 436/74; 436/164; 436/172; 422/56; 422/82.05; 422/82.06; 422/82.07; 422/82.08; 422/82.09

[58] Field of Search ........................ 422/56, 82.05–82.09; 436/73, 74, 79, 164, 172

[56] References Cited

U.S. PATENT DOCUMENTS

| | | | |
|---|---|---|---|
| 4,367,072 | 1/1983 | Vögtle et al. | 436/805 X |
| 4,645,744 | 2/1987 | Charlton et al. | 436/93 |
| 4,795,712 | 1/1989 | Toner et al. | 436/79 X |
| 4,849,362 | 7/1989 | DeMarinis et al. | 436/79 X |
| 4,859,606 | 8/1989 | Cram et al. | 436/79 |
| 4,992,381 | 2/1991 | Cram et al. | 436/79 X |
| 5,037,615 | 8/1991 | Kane | 422/82.08 |
| 5,096,832 | 3/1992 | Raban et al. | 436/79 X |
| 5,132,095 | 7/1992 | Koshiishi et al. | 422/82.07 |
| 5,154,890 | 10/1992 | Mauze et al. | 436/79 X |
| 5,262,330 | 11/1993 | Chapoteau et al. | 436/79 |
| 5,310,888 | 5/1994 | Bloczynski et al. | 436/79 X |

FOREIGN PATENT DOCUMENTS 384677 12/1987 Australia .

OTHER PUBLICATIONS

T. Rosatzin et al, *Anal. Chem.* 1992, 64, 2029–2035.

B. Tümmler et al. *J. Am. Chem. Soc.* 1979, 101, 2588–2598.

H. Bauer et al. *Angew. Chem. Int. Ed. Engl.* 1983, 22, 334–335.

H.-G. Löhr et al. *Chem. Ber.* 1985, 118, 914–921.

K. Hayakawa et al. *J. Chem. Soc. Perlein Trans.* 1 1988, 511–519.

J. Bourson et al. *J. Phys. Chem.* 1989, 93, 3871–3876.

J. Bourson et al. *J. Phys. Chem.* 1993, 97, 4552–4557.

K.H. Pannell et al. *J. Organomet. Chem*, 1975, 99, C21–C23.

K.J. Odell et al, *J. Organometal. Chem.* 1979, 168, 103–114.

M. Takagi et al. Pure & Appl. Chem. 1989, 61, 1605–1612.

*Primary Examiner*—Arlen Soderquist
*Attorney, Agent, or Firm*—Watson Cole Stevens Davis, P.L.L.C.

[57] ABSTRACT

An optical indicator for determining the activity of an ion in a sample is provided with an ionophor which is capable of selectively binding the ion to be measured. The ionophor has at least two functional groups that can form an electron donor acceptor (EDA) complex, the complex bond being broken up by the attachment of the ion to be determined. This will lead to a change in at least one of the measurable optical properties of the indicator in dependence on the activity of the ion to be measured.

5 Claims, No Drawings

OPTICAL INDICATOR FOR DETERMINING THE ACTIVITY OF AN ION IN A SAMPLE

CROSS-REFERENCE TO RELATED APPLICATION

This application is a continuation of application Ser. No. 08/306,421, filed Sep. 16, 1994, now abandoned.

BACKGROUND OF THE INVENTION

The invention relates to an optical indicator for determining the activity of an ion in a sample, the sample being at least in indirect contact with the indicator, and the indicator being provided with an ionophor capable of selectively binding the ion to be measured.

DESCRIPTION OF THE PRIOR ART

From the relevant literature various methods are known for determining charged, i.e., ionic sample constituents. With these methods it is possible to determine both chemical elements in their ionic form and charged molecules. The method most frequently employed in practice is the determination of chemical elements in their ionic form with the use of ion-sensitive electrodes (so-called ISE electrodes). This measuring technique is based on the use of ion-selective molecules which are capable of accepting certain ions at the sensor membrane in a highly specific and selective manner, thus generating a potential to be subsequently measured, amplified and finally transmitted to a display.

To determine these charged chemical elements by means of optical methods of analysis with the use of sensors (so-called optodes) is considered more difficult to this day. There are methods, for instance, where a ionophor is embedded in a membrane, and a potential-sensitive fluorophor is embedded in the same membrane, the membrane contacting a sample at its boundary, and an electrolyte from the sample being detected and bound by an ion carrier, which will lead to a change in potential at the boundary, and, consequently, in the spectroscopic properties of the potential-sensitive fluorophor. These spectroscopic properties are monitored by suitable optical measuring units and the corresponding values are determined. Such a method is described in AT-B 384 677, for example.

Another method of this type is presented in U.S. Pat. No. 4,645,744. In that case a membrane contains both an ionophor and a chromophor. The underlying principle is that an ion from the chromophor is released for charge compensation when a charged ion has been accepted by the ionophor. The liberated ion is given up to the sample. Typically, the ion is a proton. The chromophor essentially is an indicator acid which is converted to the corresponding indicator base after a proton has been given up, thereby undergoing a change in its spectroscopic properties. This method suffers from the drawback that it is only practicable with samples whose pH is precisely determined and in the ideal case is constant.

Any errors in determining the sample pH will exponentially enter into the result measured for determination of the charged chemical element, since ph=−log $[H^+]$.

SUMMARY OF THE INVENTION

It is an object of the invention to propose optical indicators which avoid the disadvantages of the known indicators described above and of the respective measuring techniques, and which should be universally employable with diverse ions while the spectroscopic parameters should be identical for these diverse types of ions.

In the invention this object is achieved by using an ionophor with at least two functional groups forming an electron donor acceptor (EDA) complex, whose conformation can be changed by the attachment of the ion to be measured—the EDA complex being broken up during this process—such that at least one of the optical properties of the indicator will undergo a measurable change.

An EDA complex always consists of a donor molecule and an acceptor molecule. The donor molecule may give up an individual electron or electron pair to a pi-orbital of a double bond or an aromatic system (aromatic hydrocarbon). The existence of an EDA complex may be proved by inspecting the electron spectrum of the complex. EDA complexes typically produce a spectrum (charge transfer spectrum) which does not correspond to the sum of individual spectra of the two individual molecules. The term conformation refers to the spatial configuration of the atoms of a molecule or molecular compound.

The two functional groups are arranged along the backbone of the molecule suitable for ion detection (ionophor) in such a way that in the absence of ions a free mobility of the backbone will permit the formation of a charge transfer complex between the two or more functional groups. If an ion is added it will form a coordinative bond with the molecular backbone of the ionophor, thus leading to a new orientation of the backbone, or rather a change in conformation such that the charge transfer complex is broken up. The spectroscopic effects of this process include a change in the spectroscopic properties of the system, i.e., new absorption- and/or fluorescence bands may be observed; absorption- and/or fluorescence bands disappear; decay time changes significantly, or other spectroscopic variables undergo a measurable change (anisotropy, circular dichroism, etc.).

When such indicator molecules are embedded in a hydrophobic matrix the interaction of the functional groups should be as small as possible, as any molecular interaction is strongly intensified in a hydophobic matrix. If a hydrophilic matrix is used it is possible to select functional groups with a higher degree of interaction.

A variant of the invention provides that both functional groups of the ionophor consist of an aromatic hydrocarbon with at least one substituent each, the at least one substituent of one functional group being an electron donor and the at least one substituent of the other functional group being an electron acceptor. The stability of these CT complexes is greatly influenced by the properties of the respective substituents. The ability of attracting electrons or giving them up to the electron system of the aromatic hydrocarbons is described by the Hammort equation. In this equation the substituent constant sigma is a leading variable indicating to which extent a substituent is electron-pulling or electron-pushing.

Another variant provides that one functional group of the ionophor have an aromatic hydrocarbon, whose at least one substituent is an electron donor, and that the other functional group of the ionophor be a heavy atom, for example chlorine, bromine, or iodine.

For measuring different ions a suitably selective ionophor may be used, the functional groups remaining the same. In this way the same spectroscopic parameters and the same excitation and measuring equipment may be employed for different ions.

The above embodiments of the invention permit the following spectroscopic variants:

(a) One functional group has a fluorophor and the other one an aromatic molecule. The charge transfer complex formed therefrom does not fluoresce. When the ionophor has accepted the ion its conformation will change such that the charge transfer complex will break up, and the absorption bands of the charge transfer complex will disappear (spectroscopically accessible), and the fluorescence of the fluorophor will reappear. In this instance fluorescence intensity will increase with the concentration of the analyte being studied. The aromatic molecule acts as a fluorescence quencher.

(b) One functional group has a fluorophor and the other one is a heavy atom (e.g., chlorine, bromine, or iodine). In the initial state the fluorescence of the fluorophor is quenched by the external heavy atom quencher. In the charged state (after the analyte's coordinative attachment to the ionophor) the heavy atom can no longer quench the fluorescence of the fluorophor. Fluorescence intensity of the fluorophor is monitored and analyzed.

(c) Formation of a classical charge transfer complex consisting of one functional group with an electron donor (acceptor) and one functional group with an electron acceptor (donor). The charge transfer complex does not fluoresce and shows long-wave absorption. When an ion is accepted by the ionophor the extinction coefficient of the complex is reduced and new absorption bands of the individual functional groups are added.

According to the invention the ions listed in the table below may be determined with the use of the following ionophors, the nomenclature and product numbers referring to products of FLUKA CHEMIE AG, CH-9470 BUCHS, Switzerland.

| ION | IONOPHOR | PRODUCT NUMBER |
|---|---|---|
| $Li^+$ | Lithium Ionophar I | 62 557 |
| $Na^+$ | Sodium Ionophor III | 71 734 |
| $Ca^{++}$ | Calcium Ionophor I | 21 192 |
| $Mg^{++}$ | Magnesium Ionophor IV | 63 088 |

The chemical name of Lithium Ionophor I (Product Number 62557) is N,N'-diheptyl-N,N',5,5-tetramethyl-3,7-dioxanonane-diamide, the chemical name of Sodium Ionophor III (Product Number 71734) is N,N,N',N'-tetracyclohexyl-1,2-phenylendioxydiacetamide, the chemical name of Calciuan Ionophor I (Product Number 21192) is (−)-(R,R)-N,N'-bis-(11-(ethoxycarbonyl)-undecyl),-N,N,-4,5-tetramethyl-3,6-dioxaoctan-diamide, and the chemical name of Magnesium Ionophor IV (Product Number 63088) is N,N',N"-tris-(3-(heptylmethylamino)-3-oxopropionyl)-8,8,-iminodioctylamine.

In the invention particularly good results are obtained if the distance of the two functional groups in the backbone of the ionophor is a minimum of four and a maximum of eight intermediate atoms.

Without intending any restriction of the invention, examples of indicator molecules measuring $Li^+$, $Na^+$, $Ca^{++}$, and $Mg^{++}$ will be given in more detail below.

In an indicator molecule for determination of the $Li^+$ activity the two functional groups are attached to the lithium ionophor at positions $R_1$ and $R_2$. The two groups are a phenytene diamine and a nitronaphthacene.

As a concrete example the substitution with p-phenylene diamine and nitronaphthacene is presented, a new CT band appearing at approx. 360 nm upon complex formation.

EXAMPLE 1

Indicator molecule with Lithium Ionophor and nitronaphthacene and phenylene diamine

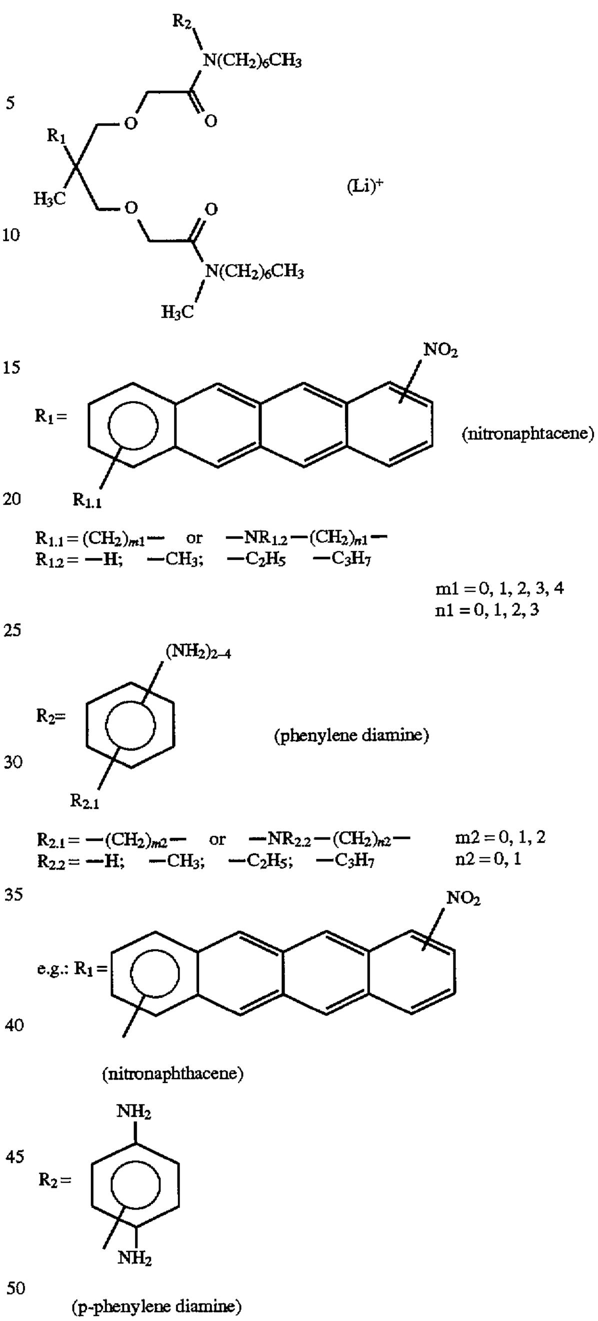

Following are indicator molecules for $Na^+$ (Examples 2 to 5), $Ca^{++}$ (Example 6), and $Mg^{++}$ (Example 7). It should be noted that the substitution sites of the functional groups are exchangeable (with the exception of Example 2). The naphthacenes may be replaced by naphthalenes and their derivatives.

EXAMPLE 2

Indicator molecule with Natrium Ionophor III and nitronaphthacene and phenylene diamine (Variant I)

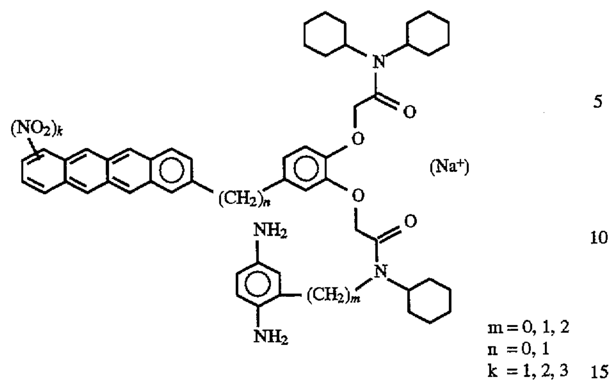

EXAMPLE 3

Indicator molecule with Natrium Ionophor III and nitronaphthacene and phenylene diamine (Variant II)

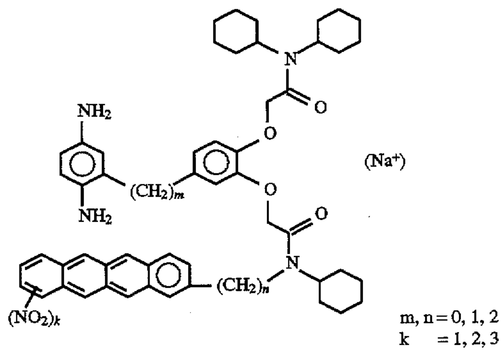

EXAMPLE 4

Indicator molecule with Natrium Ionophor III, hydroquinone as donor and p-quinone as acceptor

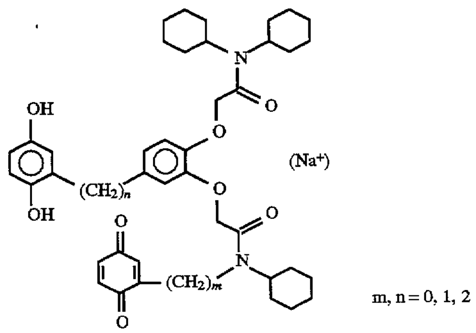

EXAMPLE 5

Indicator molecule with Natrium Ionophor III and pyrene and the heavy atom bromine

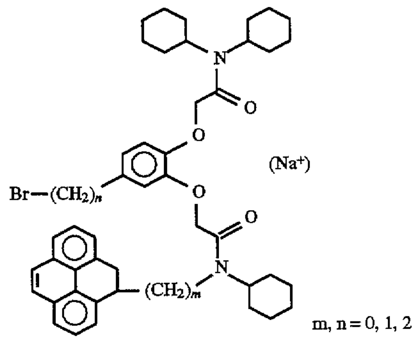

EXAMPLE 6

Indicator molecule with Calcium Ionophor and nitronaphthacene and phenylene diamine

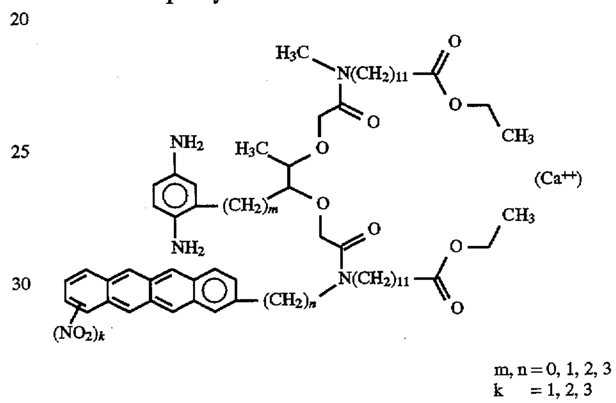

EXAMPLE 7

Indicator molecule with Magnesium Ionophor and nitronaphthacene and phenylene diamine

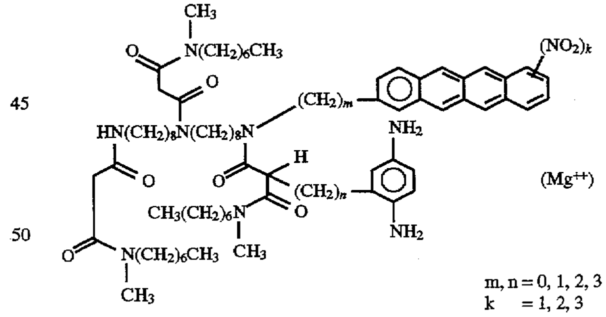

Other suitable electron acceptors are mono- to trinitrocoronene, mono-to tri-nitro naphthalene, and mono- to trinitrobenzo[ghi]perylene; electron donors include mono- to triaminobenzene, mono- to tridiamethyl aminobenzene, and mono- to trimethoxy benzene.

I claim:

1. An optical indicator for determining the activity of an ion selected from the group consisting of Li+, Na+, Ca++ and Mg++ in a sample, said sample being in at least indirect contact with said optical indicator, said optical indicator comprising molecules of an ionophor having a molecular structure including at least two functional groups which form an electron donor acceptor (EDA) complex whose conformation is changed after selectively binding with a corresponding ion, such that at least one optical property of said optical indicator will undergo a measurable change, at least one of said at least two functional groups including a fluorophor, said ionophor being selected from the group consisting of N,N'-diheptyl-N,N',5,5-tetramethyl-3,7-dioxanonane-diamide, N,N,N',N'-tetracyclohexyl-1,2-phenylendioxydiacetamide, (−)-(R,R)-N,N'-bis-(11-(ethoxycarbonyl)-undecyl),-N,N'-4,5-tetramethyl-3,6-dioxaoctan-diamide, and N,N',N"-tris-(3-(heptylmethylamino)-3-oxopropionyl)-8,8'-iminodioctylamine.

2. An optical indicator according to claim 1, wherein both of said functional groups of said ionophor consist of an aromatic hydrocarbon with at least one substituent each, said at least one substituent of a first of said functional groups being an electron donor and said at least one substituent of a second of said functional groups being an electron acceptor.

3. An optical indicator according to claim 1, wherein said ionophor includes a molecular backbone of bonded atoms and wherein a distance between said two functional groups relative to said backbone is between four and eight of said bonded atoms.

4. An optical indicator for determining the activity of an ion selected from the group consisting of Li+, Na+, Ca++ and Mg++ in a sample, said sample being in at least indirect contact with said optical indicator, said optical indicator comprising molecules of an ionophor having a molecular structure including at least two functional groups which form an electron donor acceptor (EDA) complex whose conformation is changed after selectively binding with a corresponding ion, such that at least one optical property of said optical indicator will undergo a measurable change, one of said functional groups having an aromatic hydrocarbon with at least one substituent which is an electron donor, and another of said functional groups is an atom from the group consisting of chlorine, bromine and iodine, said ionophor being selected from the group consisting of N,N'-diheptyl-N,N',5,5-tetramethyl-3,7-dioxanonane-diamide, N,N,N',N'-tetracyclohexyl-1,2-phenylendioxydiacetamide, (−)-(R,R)-N,N'-bis-(11-(ethoxycarbonyl)-undecyl),-N,N'-4,5-tetramethyl-3,6-dioxaoctan-diamide, and N,N',N"-tris-(3-(heptylmethylamino)-3-oxopropionyl)-8,8'-iminodioctylamine.

5. An optical indicator according to claim 4, wherein said ionophor includes a molecular backbone of bonded atoms and wherein a distance between said two functional groups relative to said backbone is between four and eight of said bonded atoms.

* * * * *